(12) United States Patent
Mackie et al.

(10) Patent No.: US 9,490,099 B2
(45) Date of Patent: Nov. 8, 2016

(54) SYSTEM AND METHOD FOR MULTI-SOURCE X-RAY-BASED IMAGING

(71) Applicant: Wisconsin Alumni Research Foundation, Madison, WI (US)

(72) Inventors: Thomas R. Mackie, Verona, WI (US); Brandon J. Walker, Madison, WI (US); Jonathon R. Seaton, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 63 days.

(21) Appl. No.: 14/463,881

(22) Filed: Aug. 20, 2014

(65) Prior Publication Data
US 2016/0056008 A1      Feb. 25, 2016

(51) Int. Cl.
*H01J 35/30* (2006.01)
*H01J 35/04* (2006.01)
*A61B 6/03* (2006.01)
*A61B 6/00* (2006.01)
*H01J 35/06* (2006.01)
*H01J 35/12* (2006.01)
(Continued)

(52) U.S. Cl.
CPC .......... *H01J 35/045* (2013.01); *A61B 6/032* (2013.01); *A61B 6/035* (2013.01); *A61B 6/06* (2013.01); *A61B 6/4007* (2013.01); *A61B 6/4014* (2013.01); *A61B 6/4021* (2013.01); *A61B 6/4488* (2013.01); *H01J 35/00* (2013.01); *H01J 35/06* (2013.01); *H01J 35/12* (2013.01); *H01J 35/14* (2013.01); *A61B 6/405* (2013.01); *H01J 2235/068* (2013.01); *H01J 2235/1204* (2013.01); *H01J 2235/127* (2013.01)

(58) Field of Classification Search
CPC .......... H01J 35/065; H01J 2235/068; H01J 2235/062
See application file for complete search history.

(56) References Cited

U.S. PATENT DOCUMENTS

| | | | |
|---|---|---|---|
| 4,282,438 A | 8/1981 | Nishida et al. | |
| 4,521,901 A | 6/1985 | Rand | |

(Continued)

FOREIGN PATENT DOCUMENTS

| | | |
|---|---|---|
| CN | 202051718 U | 11/2011 |
| CN | 102370494 A | 3/2012 |

(Continued)

OTHER PUBLICATIONS

Baek, et al., A Multi-Source Inverse-Geometry CT System: Initial Results With an 8 Spot X-ray Source Array, Physics in Medicine and Biology, 2014, 59:1189-1202.

(Continued)

*Primary Examiner* — Hoon Song
(74) *Attorney, Agent, or Firm* — Quarles & Brady, LLP

(57) ABSTRACT

An imaging module includes a plurality of cathodes and respective gates, each cathode configured to generate a separate beam of electrons directed across a vacuum chamber and each gate matched to at least one respective cathode to enable and disable each separate beam of electrons from being directed across the vacuum chamber. A target anode is fixed within the vacuum chamber and arranged to receive the separate beam of electrons from each of the plurality of cathodes and, therefrom, generate a beam of x-rays. A deflection system is arranged between the plurality of cathodes and the target anode to generate a variable magnetic field to control a path followed by each of the separate beams of electrons to the target anode.

24 Claims, 7 Drawing Sheets

(51) Int. Cl.
*H01J 35/14* (2006.01)
*A61B 6/06* (2006.01)
*H01J 35/00* (2006.01)

(56) References Cited

U.S. PATENT DOCUMENTS

| | | | |
|---|---|---|---|
| 5,604,778 A | 2/1997 | Polacin et al. | |
| 5,966,422 A | 10/1999 | Dafni et al. | |
| 6,125,167 A * | 9/2000 | Morgan | H01J 35/10 378/121 |
| 6,873,677 B2 | 3/2005 | Kaufman | |
| 6,983,035 B2 | 1/2006 | Price et al. | |
| 7,197,115 B2 | 3/2007 | Unger et al. | |
| 7,545,901 B2 | 6/2009 | Mistretta | |
| 7,548,604 B2 | 6/2009 | De Man et al. | |
| 7,627,081 B2 | 12/2009 | Bontus | |
| 7,639,785 B2 | 12/2009 | Kirshner et al. | |
| 7,649,973 B1 | 1/2010 | Li et al. | |
| 7,813,478 B2 | 10/2010 | Nisius | |
| 7,835,488 B2 | 11/2010 | Heuscher et al. | |
| 7,903,789 B2 | 3/2011 | Morton et al. | |
| 7,929,659 B2 | 4/2011 | Wu et al. | |
| 7,983,384 B2 | 7/2011 | Hampel et al. | |
| 8,031,829 B2 | 10/2011 | Yin et al. | |
| 8,284,896 B2 | 10/2012 | Singh | |
| 8,295,442 B2 | 10/2012 | Caiafa et al. | |
| 8,320,519 B2 | 11/2012 | Ribbing et al. | |
| 8,483,351 B2 | 7/2013 | Wang et al. | |
| 8,509,387 B2 | 8/2013 | Tsujii et al. | |
| 8,571,176 B2 | 10/2013 | Ikhlef et al. | |
| 2005/0025280 A1 | 2/2005 | Schulte | |
| 2006/0018432 A1* | 1/2006 | Zhou | A61B 6/032 378/122 |
| 2008/0137805 A1 | 6/2008 | Forster et al. | |
| 2009/0190719 A1 | 7/2009 | Barschdorf et al. | |
| 2009/0238328 A1 | 9/2009 | Forthmann et al. | |
| 2010/0074392 A1* | 3/2010 | Behling | H01J 35/06 378/4 |
| 2011/0142201 A1 | 6/2011 | Eberhard et al. | |
| 2011/0188724 A1 | 8/2011 | Bruder et al. | |
| 2012/0219116 A1 | 8/2012 | Thompson et al. | |
| 2012/0230464 A1 | 9/2012 | Ling et al. | |
| 2012/0257710 A1 | 10/2012 | Funk | |
| 2012/0269317 A1 | 10/2012 | Fritzler et al. | |
| 2013/0202080 A1 | 8/2013 | Yu et al. | |
| 2013/0294666 A1 | 11/2013 | Bultema | |
| 2013/0308746 A1 | 11/2013 | Ueki | |
| 2013/0343509 A1 | 12/2013 | Gregerson et al. | |
| 2014/0086380 A1 | 3/2014 | Song et al. | |
| 2014/0185739 A1 | 7/2014 | Tang et al. | |

FOREIGN PATENT DOCUMENTS

| | | |
|---|---|---|
| CN | 102519989 A | 6/2012 |
| CN | 203083952 U | 7/2013 |
| CN | 103505231 A | 1/2014 |
| CN | 103505233 A | 1/2014 |
| JP | 2012187180 A | 10/2012 |
| WO | 2009115982 A1 | 9/2009 |
| WO | 2011033439 A1 | 3/2011 |
| WO | 2013111041 A1 | 8/2013 |
| WO | 2013184103 A1 | 12/2013 |
| WO | 2014028930 A1 | 2/2014 |
| WO | 2014047518 A1 | 3/2014 |

OTHER PUBLICATIONS

Xu, et al., A Tetrahedron Beam Computed Tomography Benchtop System With a Multiple Pixel Field Emission X-ray Tube, Med. Phys., 2011, 38(10):5500-5508.
PCT International Search Report and Written Opinion, PCT/US2015/045895, Dec. 4, 2015.

* cited by examiner

SYSTEM AND METHOD FOR MULTI-SOURCE X-RAY-BASED IMAGING

GOVERNMENT RIGHTS

N/A.

BACKGROUND

The present disclosure relates generally to systems and methods for imaging a subject and, in particular, to systems and methods for performing imaging processes using x-rays delivered from multiple sources.

X-ray-based imaging, including so-called "x-ray imaging" and computed tomography (CT) imaging, are some of the most common diagnostic imaging modality used in modern medicine, enabling rapid, non-invasive image acquisition at high resolution. As shown in the example diagram of FIG. 1A, conventional CT systems 10 generally include a gantry 12 fitted with a X-ray tube 14 or at most, two X-ray tubes for systems currently in clinical use and opposing detector assembly 16, which, together, rotate about a subject 18 arranged on a patient bed 20 to acquire multiple projections for reconstructing an image. That is, the X-ray tube 14 and detector assembly 16 arranged opposite the X-ray tube 14 are affixed to the gantry 12 and rotate together with the gantry 12 about the subject 18. As illustrated in the picture of FIG. 1B, this system 10 is complex and requires heavy and sophisticated control hardware and electronics.

The x-ray source 14 projects an x-ray beam 22, which may be a fan-beam or cone-beam of x-rays, towards the detector array 16 on the opposite side of the gantry 12. The detector array 16 includes a number of x-ray detector elements 24. Together, the x-ray detector elements 24 sense the projected x-rays 22 that pass through a subject 18, such as a medical patient or an object undergoing examination, who is positioned in the CT system 10. Each x-ray detector element 24 produces an electrical signal that may represent the intensity of an impinging x-ray beam and, hence, the attenuation of the beam as it passes through the subject 18. In some configurations, each x-ray detector 24 is capable of counting the number of x-ray photons that impinge upon the detector 24. During a scan to acquire x-ray projection data, the gantry 12 and the components mounted thereon rotate about a center of rotation 26 located within the CT system 10.

The CT system 10 also includes an operator workstation 28, which typically includes a display 30; one or more input devices 32, such as a keyboard and mouse; and a computer processor 34. The computer processor 34 may include a commercially available programmable machine running a commercially available operating system. The operator workstation 28 provides the operator interface that enables scanning control parameters to be entered into the CT system 10. In general, the operator workstation 28 is in communication with a data store server 36 and an image reconstruction system 38. By way of example, the operator workstation 28, data store sever 36, and image reconstruction system 38 may be connected via a communication system 40, which may include any suitable network connection, whether wired, wireless, or a combination of both. As an example, the communication system 40 may include both proprietary or dedicated networks, as well as open networks, such as the internet.

The operator workstation 28 is also in communication with a control system 42 that controls operation of the CT system 10. The control system 42 generally includes an x-ray controller 44, a table controller 46, a gantry controller 48, and a data acquisition system 50. The x-ray controller 44 provides power and timing signals to the x-ray source 14 and the gantry controller 48 controls the rotational speed and position of the gantry 12 by controlling operation of a motor 68. The table controller 46 controls a table 20 to position the subject 18 in the gantry 12 of the CT system 10.

The DAS 50 samples data from the detector elements 24 and converts the data to digital signals for subsequent processing. For instance, digitized x-ray data is communicated from the DAS 50 to the data store server 36. The image reconstruction system 38 then retrieves the x-ray data from the data store server 36 and reconstructs an image therefrom. The image reconstruction system 38 may include a commercially available computer processor, or may be a highly-parallel computer architecture, such as a system that includes multiple-core processors and massively parallel, high-density computing devices. Optionally, image reconstruction can also be performed on the processor 34 in the operator workstation 28. Reconstructed images can then be communicated back to the data store server 36 for storage or to the operator workstation 28 to be displayed to the operator or clinician.

The x-ray source 14 is a tube assembly that includes a housing unit 52, a coolant path and/or pump 54, cathode end 56, an anode end 58, and a center section 60 positioned between the cathode end 56 and the an anode end 58, which contains an x-ray tube 62. The x-ray tube 62 is enclosed in a fluid chamber 64 within lead-lined casing 66. The chamber 64 is typically filled with fluid, such as dielectric oil, but other fluids including water or air may be utilized. The fluid circulates through housing 52 to cool the x-ray tube 62 and may insulate a casing 64 from high electrical charges within the x-ray tube 62.

Though CT systems provide desirable contrast and flexibility to facilitate a wide-variety of clinical analysis, it relies upon ionizing radiation. Thus, a further constraint on the design and manufacturing of CT systems is the ability to control or adapt the dose of radiation received by the subject 18 by way of the x-ray beam 22. For example, filters, such as so-called "bowtie" filters 70, have long been utilized to sculpt the x-ray beam 22 and, thereby, control the dose received by the patient. Some filters, such as the illustrated bowtie filter 70, have been coupled with control systems and/or motors 72 to allow the filtering achieved by the bowtie filter 70 to be adjusted.

All these complex components associated with the x-ray source 14 and detector array 16 must be designed to rotate with the gantry 12. The motor 68 must be capable of applying a large torque to the large gantry 12 to accelerate the gantry 12 to a high constant rate of rotation in a short time. As an indication of the speeds which are reached, sufficient data to produce an image can be collected in less than one second. Since the rotational inertia of this apparatus increases with distance from the center of rotation 26, rotation of the gantry 12, which includes the x-ray tube 14 and detectors 16 and all associated hardware and, thus, has a large inertia, requires the motor 66 to deliver extremely high torques. Furthermore, all components of the gantry 12 must be able to withstand these forces during operation and repeated rotational starts and stops. Accordingly, CT systems are generally complex and carry very-high manufacturing and maintenance costs.

All of these and other control and programming capabilities add to the complexity and costs to these systems. As such, the trend toward greater and greater complexity of CT systems continues and, in particular, is prevalent when one considers the components and systems coupled to the gantry 12. As but one example, consider the increasing availability of dual-source CT systems. In such dual-source systems, as illustrated, the above described components associated with the gantry 12, such as the x-ray source 14, detector array 16, and the like, are doubled. Thus, the complexity of the gantry systems 12 doubles, which further increases the underlying costs of the system and the maintenance requirements.

Therefore, given the above, there is a need for systems capable of fast and accurate computed tomography imaging that is not so limited by the complexity and the costs associated with the complexity of traditional CT systems.

SUMMARY

The present invention overcomes the aforementioned drawbacks by providing a system for computed tomography (CT) imaging implementing a modular design including multiple x-ray sources. More particularly, a multi-source x-ray tube is provided that is able to deliver high current from an arbitrary number of focal spots. The system may include a fixed number of electron beams that are electromagnetically swept over a cooled target. Utilizing a modular design, the x-ray tubes can be arranged in a variety of configurations to suit a particular application. Using this design, unique scanning and radiation control techniques can be implemented, including rotation-free CT imaging, multi-energy imaging, and virtual filtering. Furthermore, active cooling of components is available in any given module.

In accordance with one aspect of the disclosure, an imaging system is provided that includes a platform for receiving a subject to be imaged using the imaging system and a source module arranged to deliver a beam of ionizing radiation to the subject. The source module includes a vacuum chamber and a plurality of cathodes and respective gates, each cathode configured to generate a separate beam of electrons directed across the vacuum chamber and each gate matched to at least one respective cathode to enable and disable each separate beam of electrons from being directed across the vacuum chamber. The source module also includes a target anode arranged to receive the separate beam of electrons from each of the plurality of cathodes and, therefrom, generate the beam of ionizing radiation and a deflection system arranged between the plurality of cathodes and the target anode to generate a variable magnetic field to control a path followed by each of the separate beams of electrons to the target anode. A controller is configured to control operation of the plurality of cathodes and respective gates to selectively enable and disable each separate beam of electrons from being directed across the vacuum chamber and control operation of the deflection system to change the path followed by each of the separate beam of electrons to the target anode based on at least one of a heating of the target anode caused by the beam of electrons and a view angle of the subject to be achieved using the ionizing radiation.

In accordance with another aspect of the disclosure, an imaging system is provided that includes a bore for receiving a subject to be imaged using the imaging system and a plurality of source modules arranged about the bore to deliver a beam of x-rays to a subject to be imaged. Each source module includes a vacuum chamber and a plurality of cathodes and respective gates, each cathode configured to generate a separate beam of electrons directed across the vacuum chamber and each gate matched to at least one respective cathode to enable and disable each separate beam of electrons from being directed across the vacuum chamber. Each source module also includes a target anode arranged to receive the separate beam of electrons from each of the plurality of cathodes and, therefrom, generate the beam of x-rays and a deflection system arranged between the plurality of cathodes and the target anode to generate a variable magnetic field to control a path followed by each of the separate beams of electrons to the target anode. A controller is configured to control operation of the plurality of cathodes and respective gates to selectively enable and disable each separate beam of electrons from being directed across the vacuum chamber and control operation of the deflection system to change the path followed by each of the separate beam of electrons to the target anode based on at least one of a heating of the target anode caused by the beam of electrons and a view angle of the subject to be achieved using the beam of x-rays. A plurality of detectors is arranged in opposition to a respective one of the plurality of source modules across the bore to receive the beam of x-rays and assembled medical imaging data based thereon.

In accordance with yet another aspect of the disclosure, a source module is provided for generating x-rays that includes a vacuum chamber. The source module also includes a plurality of cathodes and respective gates, each cathode configured to generate a separate beam of electrons directed across the vacuum chamber and each gate matched to at least one respective cathode to enable and disable each separate beam of electrons from being directed across the vacuum chamber. The source module further includes a target anode fixed within the vacuum chamber and arranged to receive the separate beam of electrons from each of the plurality of cathodes and, therefrom, generate a beam of x-rays. The source module also includes a deflection system arranged between the plurality of cathodes and the target anode to generate a variable magnetic field to control a path followed by each of the separate beams of electrons to the target anode to selectively sweep across the target anode and, thereby, change a point of impact of each separate beam of electrons with the target anode and change a location of the beam of x-rays generated.

The foregoing and other advantages of the invention will appear from the following description.

DETAILED DESCRIPTION

Figure 1A:
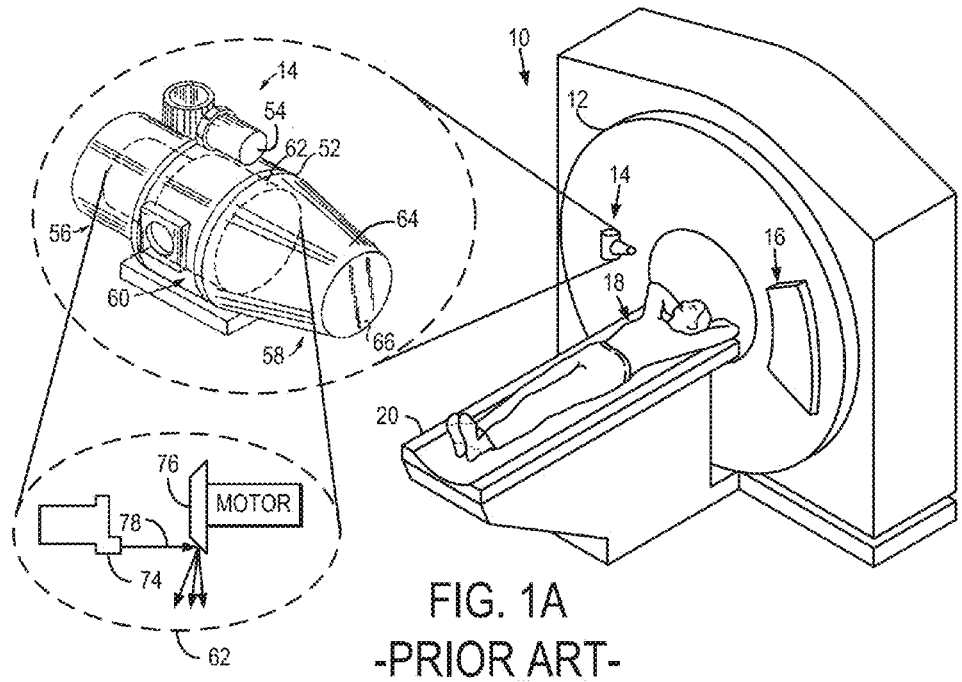
FIGS. 1A and 1B are perspective and schematic block diagrams, respectively, of a conventional rotating-gantry CT system.
Figure 1B:
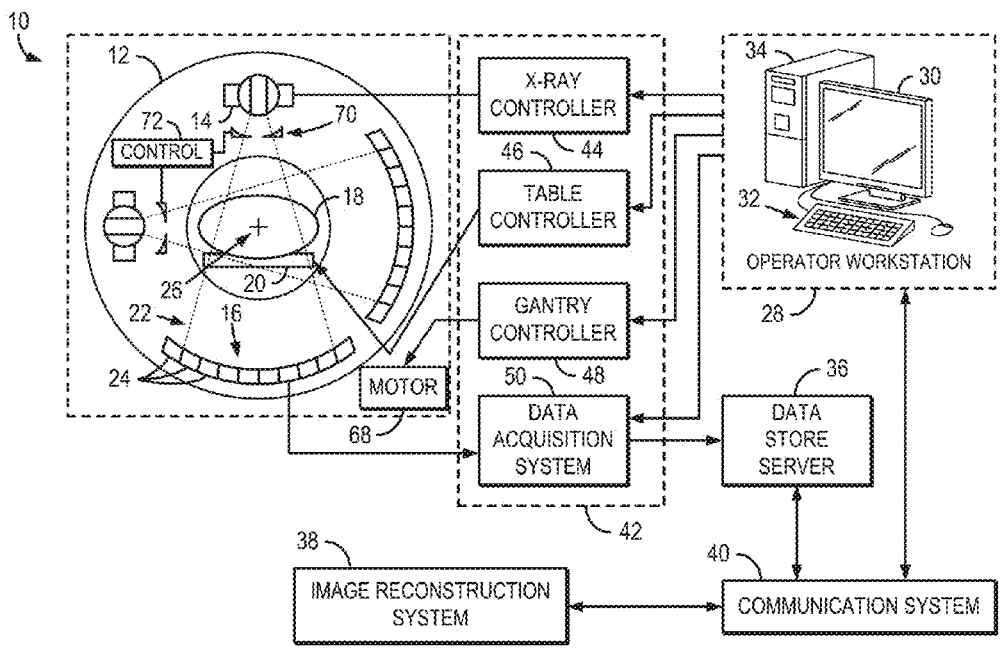

Referring to FIG. 1A, the x-ray tube 62 used in computed tomography (CT) systems 10 has, essentially, remained unchanged over the past 80 years. The modern x-ray tube 62 has a single cathode 74 that emits electrons towards a rotating anode 76. In CT scanning, two rotations are involved. First a rotation of the target anode 76 inside the tube and a rotation of the whole x-ray tube 62 on the gantry 12 about the patient 18. The target anode 76 must rotate extremely fast in order to avoid melting the x-ray tube 62 because there is only a single electron beam 78 constantly directed toward the same spot on the anode 76. This requirement for a rotating target anode 76 makes the standard x-ray tube 62 quite complex and difficult to build. The reliance on a single electron beam 78 means that the entire x-ray tube 62 must be rotated around the patient 18 with the gantry 12 for a complete CT scan. This introduces costs associated with a rotating gantry 12, and mechanical challenges with rotating fast enough to avoid image blur. Furthermore, utilization of a single source tube 62 has held back new imaging techniques that offer the potential to lower dose to the patient and, instead, has caused further reliance upon adding complex mechanical systems to control dose, such as bowtie filters 70 and associated controls 72. As will be described, the present disclosure breaks from the traditional CT systems that rely on complex rotations components to achieve the desired functionality and, instead, presents a practical multi-source x-ray tube that enables faster imaging, dose reduction, and improved image quality.

Figure 2A:
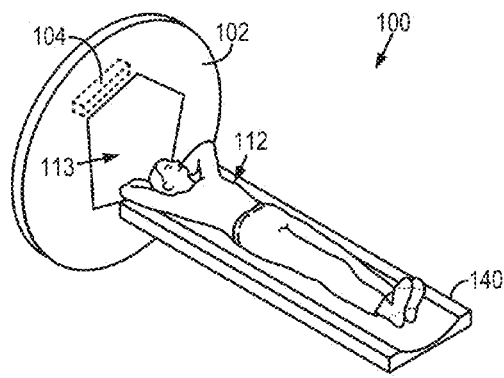
FIGS. 2A and 2B are perspective and schematic block diagrams, respectively, of a CT system configured in accordance with the present disclosure.
Figure 2B:
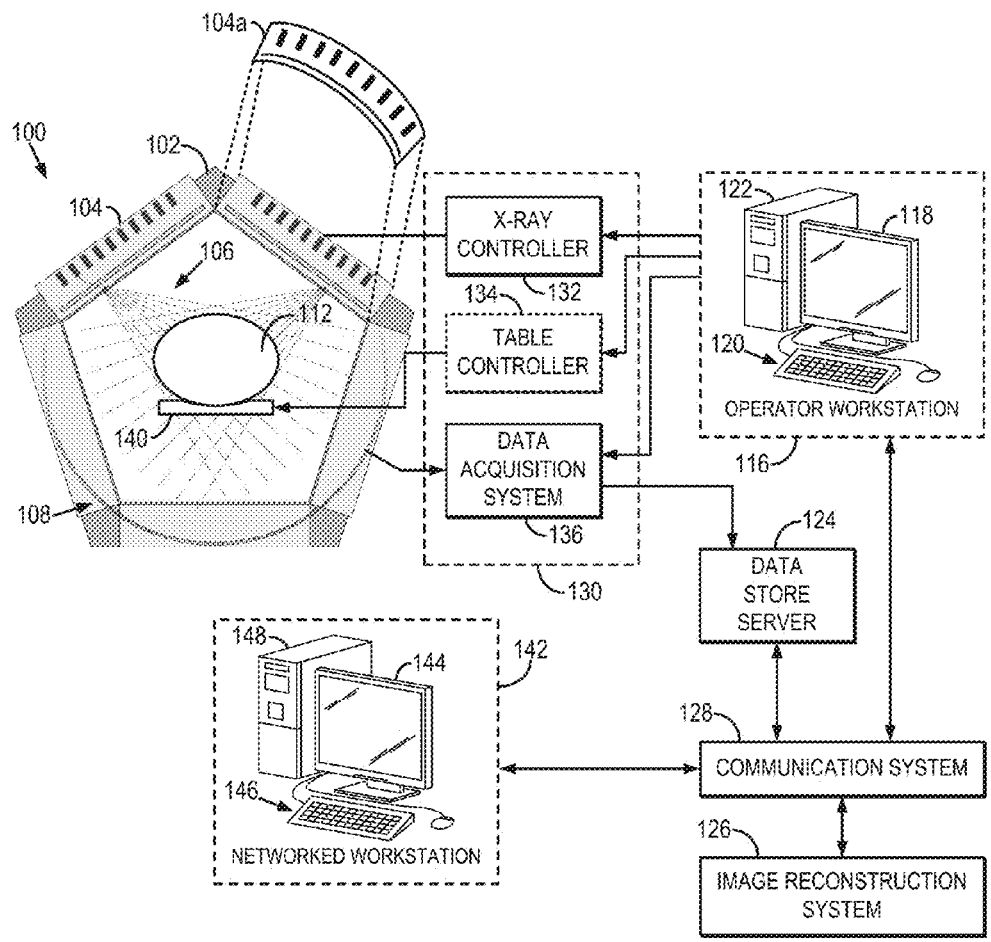

Referring now to FIGS. 2A and 2B, an example of a CT imaging system 100 in accordance with the present disclosure is illustrated. The CT system 100 includes a frame 102, to which at least one x-ray source module 104 is coupled. As illustrated, the x-ray source module 104 may be linear in shape. However, as illustrated in FIG. 2B, the x-ray source module 104 may have a non-linear shape. For example, as illustrated in FIG. 2B, the x-ray source module 104a may have an arc-like shape or other geometry, for example, to create a rounded array that arcs about the subject 112 or iso-center of the CT system 100. The x-ray source module 104 projects an x-ray beam 106 towards a detector(s) 108. The detector 108 senses the projected x-rays 106 that pass through a subject 112, such as a medical patient or an object undergoing examination, that is positioned in the CT system 100. In some configurations, each detector 108 includes elements capable of counting the number of x-ray photons that impinge upon the detector 108.

The CT system 100 also includes an operator workstation 116, which typically includes a display 118; one or more input devices 120, such as a keyboard and mouse; and a computer processor 122. The computer processor 122 may include a commercially available programmable machine running a commercially available operating system. The operator workstation 116 provides the operator interface that enables scanning control parameters to be entered into the CT system 100. In general, the operator workstation 116 is in communication with a data store server 124 and an image reconstruction system 126. By way of example, the operator workstation 116, data store sever 124, and image reconstruction system 126 may be connected via a communication system 128, which may include any suitable network connection, whether wired, wireless, or a combination of both. As an example, the communication system 128 may include both proprietary or dedicated networks, as well as open networks, such as the internet.

The operator workstation 116 is also in communication with a control system 130 that controls operation of the CT system 100. The control system 130 generally includes an x-ray controller 132, a table controller 134, and a data acquisition system (DAS) 136. The x-ray controller 132 provides power and timing signals to the x-ray module(s) 104 to effectuate delivery of the x-ray beam 106. The table controller 134 controls a table or platform 140 to position the subject 112 with respect to the CT system 100.

The DAS 136 samples data from the detector 108 and converts the data to digital signals for subsequent processing. For instance, digitized x-ray data is communicated from the DAS 136 to the data store server 124. The image reconstruction system 126 then retrieves the x-ray data from the data store server 124 and reconstructs an image therefrom. The image reconstruction system 126 may include a commercially available computer processor, or may be a highly parallel computer architecture, such as a system that includes multiple-core processors and massively parallel, high-density computing devices. Optionally, image reconstruction can also be performed on the processor 122 in the operator workstation 116. Reconstructed images can then be communicated back to the data store server 124 for storage or to the operator workstation 116 to be displayed to the operator or clinician.

The CT system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 116, or in a different facility, such as a different healthcare institution or clinic.

The networked workstation 142, whether within the same facility or in a different facility as the operator workstation 116, may gain remote access to the data store server 124 and/or the image reconstruction system 126 via the communication system 128. Accordingly, multiple networked workstations 142 may have access to the data store server 124 and/or image reconstruction system 126. In this manner, x-ray data, reconstructed images, or other data may exchanged between the data store server 124, the image reconstruction system 126, and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

As described, there has been a major push for lowering dose in CT and other imaging modalities that use ionizing radiation. Recognizing that equal radiation intensity is not needed across the entire field of view, people have developed filters, such as the above-described bowtie filter to control dose. That is, because the patient is thicker in the middle compared to the periphery, more radiation is needed in the center of the field of view to yield a sufficient signal to noise ratio. A bowtie filter is traditionally used today to limit the dose to the peripheral edges of the field of view, but this filter is of generic shape that is applied to every patient. One problem is that the beam spectrum varies considerably due to the attenuation of the bowtie shape. In addition, dose should be optimized on a per patient basis, with the ability to modulate the dose across the field of view.

Figure 3:
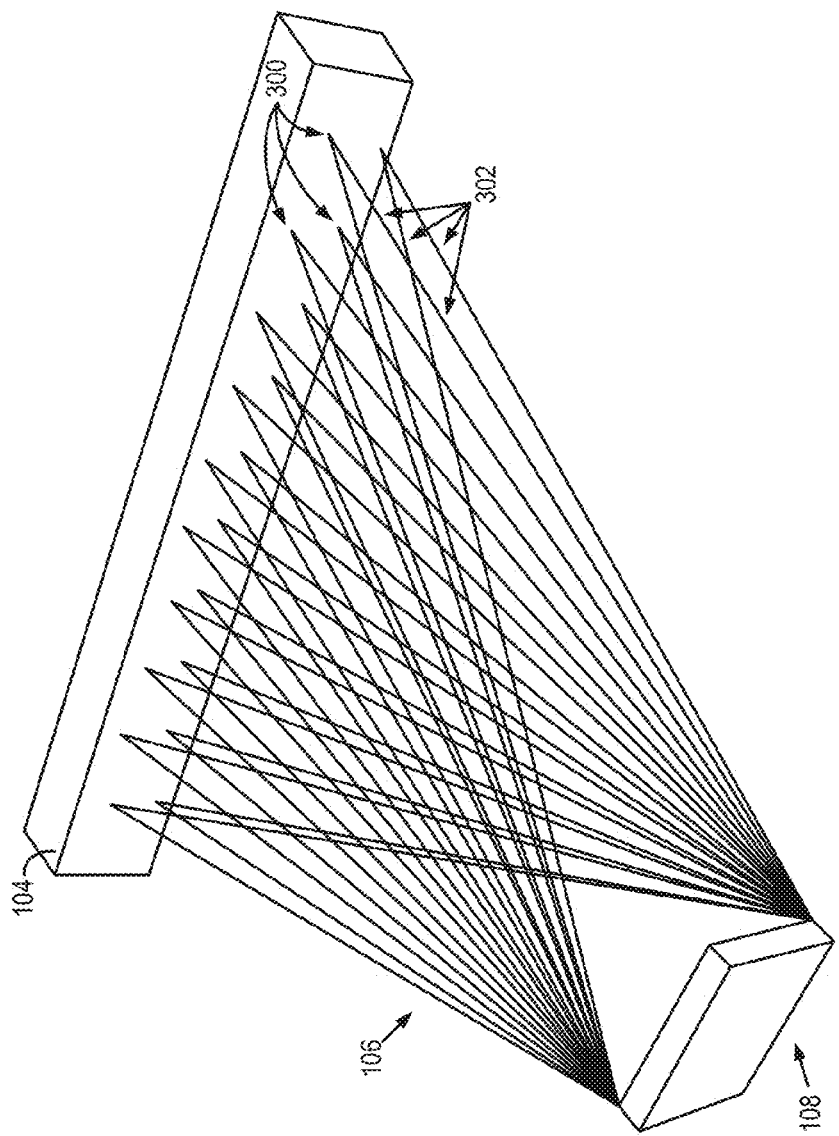
FIG. 3 is a perspective illustration of a source and detector system in accordance with the present disclosure illustrating a virtual bowtie functionality.

Referring to FIG. 3, an x-ray source module 104 in accordance with the present disclosure is illustrated in further detail. As described, the x-ray source module 104 is arranged to deliver x-ray beam 106 towards a detector 108 with the subject 112 being imaged arranged therein. A collimator may be coupled to the detector 108 that is matched to the source location and geometry. As is illustrated, in accordance with the present disclosure, the x-ray source module 104 includes multiple sources 300 (i.e., is a multi-source module) and the source module 104 and detector 108 may be fixed relative to one another. Thus, collimation may be specifically tailored to the location and geometry of the source module 104.

The multi-source x-ray tube module 104 enables the creation of a "virtual" bowtie filter, in which multiple small x-ray beams 302 are used to deliver a desired or optimized dose to a given region of the subject 112 to provide desired image quality while controlling or minimizing dose and without differential hardening of the spectrum. As will be further described, the x-ray beams 302 may be modulated in time, energy, or intensity and this modulation may take into account, among other things, the patient size, shape, or geometry.

Over the past 10 years, CT manufacturers have worked to create larger detectors with many rows of individual detector elements in an effort to increase the longitudinal coverage of a single scan. This increase in the number of detector rows allows for imaging of an entire organ, for example, the heart, in a single rotation of the gantry of the CT system. However, such a large detector leads to increased scatter radiation being picked up by the detector and yields images with greater artifacts.

As illustrated in FIG. 3, it is contemplated that the present disclosure may utilize a "inverse geometry" when compared to these traditional CT systems. That is, the multi-source x-ray tube module 104 may extend over a given distance, D, and be coupled with a comparatively small detector 108 that extends over a given distance, d, where D>>d. As will be further detailed, the multi-source x-ray tube module 104 and its ability to deliver multiple small x-ray beams 302 that are directed toward the subject 112 along a path toward the comparatively small detector 108. In this way, the multi-source x-ray tube module 104 and comparatively small detector 108 are able to image the same large volume as a traditional CT system with a very large detector (e.g., d=>D), but without the artifacts traditionally encountered.

As will be described, the multi-source x-ray tube module 104 can be used in this inverse geometry to improve image quality and even lower dose by the use of a virtual bowtie filter. That is, as will be described, the multi-source x-ray tube module 104 enables a continuously variable/selectable number of source positions and does not need to be rotated around the patient, if multiple modules are used.

Figure 4:
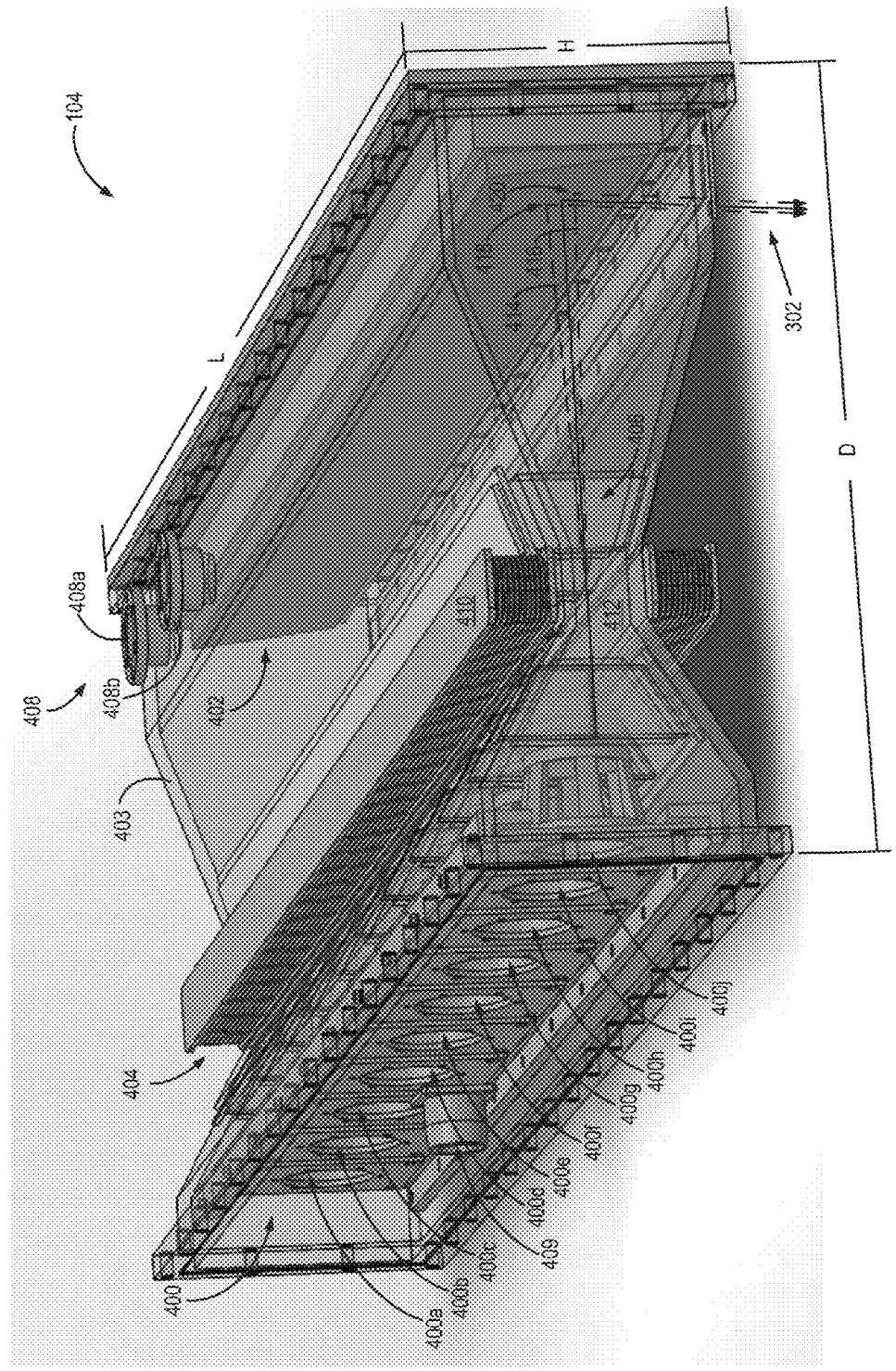
FIG. 4 is a perspective illustration of a source module in accordance with the present disclosure.

Referring to FIGS. 3 and 4, one configuration for the multi-source x-ray tube module 104 is illustrated in detail. The module 104 extends generally, from a plurality of cathodes 400 (400a-400j) to a anode/target 402. As illustrated, the anode target 402 may be shaped as an elongated pane and have a tapered surface that directs x-rays 302 away from the anode target 402 generally orthogonally to the path of the beam 406 and, as illustrated in FIG. 3, toward a subject being imaged. As one non-limiting example, the target 402 may have 7 degree angle to create a fan beam of x-rays.

A large voltage exists between the electron emitting cathodes 400 and the target 402, which is capable of accelerating the electrons to high energy. The cathodes 400 and target 402 are arranged in a vacuum chamber 403. Also, the magnets may be placed outside the vacuum chamber 403. Upon impact with the target 402, the electrons produce an x-ray spectrum 302.

The chamber 403 may be adapted into a variety of configurations. As illustrated, the chamber 403 has a length (L), a depth (D), and a height (H). In at least some configurations, the length (L) may be approximately twice the height (H). This may advantageous to protect against requiring very-large voltage sweeps and to maintain modularity.

That is, as illustrated in FIG. 2B, in CT applications where it is desirable to arrange a plurality of modules 104 about the subject 112, this dimensional configuration aids with arranging the modules 104 about a bore 13 to receive the subject 112 and allows the modules 104 surrounding the bore 113 to total an odd number, which advantageously protects against missing data. As noted above with respect to FIG. 2B, the multi-source x-ray tube module 104a may have a non-linear shape. If adapted into a non-linear shape, the multi-source x-ray tube module 104a will include a chamber 403 that is non-linear, for example, arcuate.

Arranged therebetween is a deflection system 404 that may include one or more deflection coils or other systems for controlling the path of a beam 406 as it travels from the cathode 400 to the target 402. The deflection system 404 may include one or more electromagnets 410, 412 that create a controllable and variable magnetic field. If the multi-source x-ray tube module 104a is formed in a non-linear geometry, the deflection system 404 will likewise include a complementary geometry. The magnetic deflection system 404 can be a relatively a low magnetic field system. As one non-limiting example, the magnetic field may be under 1 k gauss. As a further non-limiting example, a magnetic field of only 100 gauss can be used to obtain the necessary deflection of an electron beam in vacuum using an electron energy of 30 keV, and an electric field of 80 kV/10 cm placed perpendicular to the magnetic field. Transverse motion of approximately 8 cm is possible over a longitudinal distance of only 10 cm.

The magnets 410, 412 may be placed outside the chamber 403 to keep the chamber small and simplify manufacturing and magnetic shielding may be used to limit the deflection region. The magnet 410, 412 may be solenoid electromagnets, with the option to route the flux through a dee connecting the two. Iron or mu-metal beams in the tube may be used to ensure structural integrity and also shield the electron beam from the magnetic field outside the deflection region.

As will be further detailed, the deflection system 404 can effectuate a sweeping of multiple electron beams 406 across the target 402, in effect creating a multitude of additional locations where x-rays can be generated upon the target 402. Consequently, the electron beam 406 may be scanned horizontally across a length (L) of the target 402 and, thereby, across the gaps between electron emitting cathodes 400 to create a continuously variable x-ray source. Additionally or alternatively, the electron beam 406 may be moved vertically along a height (H) of the target 402 to further control the direction and location of the resulting x-ray beam 302 and to allow strategic selection of the point of impact of the electron beam 406 with the target 402, as will be described, to further control heating and cooling of the target 402. The electronic switching of the cathodes 400 and magnetic sweeping controls effectuated by the deflection system 404 enable x-rays to be generated around the patient in rapid succession. This technique is significantly faster than the mechanical motion of a rotating gantry.

The magnetic deflection system 404 controls the path of the beam 406 and the location of impact with the target 402. As such, the magnetic deflection system 404 can control the path the beam 406 follows to avoid hitting the same location on the target repeatedly. This range about the direct path allows the target 402 to cool at a given location before a subsequent impact, without rotation of the target 402. As noted above, though multiple cathodes 400a-400j can be used, the total number can be controlled or reduced because the magnetic deflection system 404 spreads the range of spot positions on the target 402. That is, instead of relying on the position of the cathode 400a-400j to dictate the position of spot position on the target 402 and the relative position of the x-ray spectrum 302, the magnetic deflection system 404 can be used to control spot position and direction/location of the x-ray spectrum. As an example, by controlling the magnetic fields associated with the electromagnets 410, 412, the beam 406 can be caused to move toward a first path 414 or a second path 416 and, as such, change the spot position on the target 402 between a first spot 418 and a second spot 420.

Figure 5:
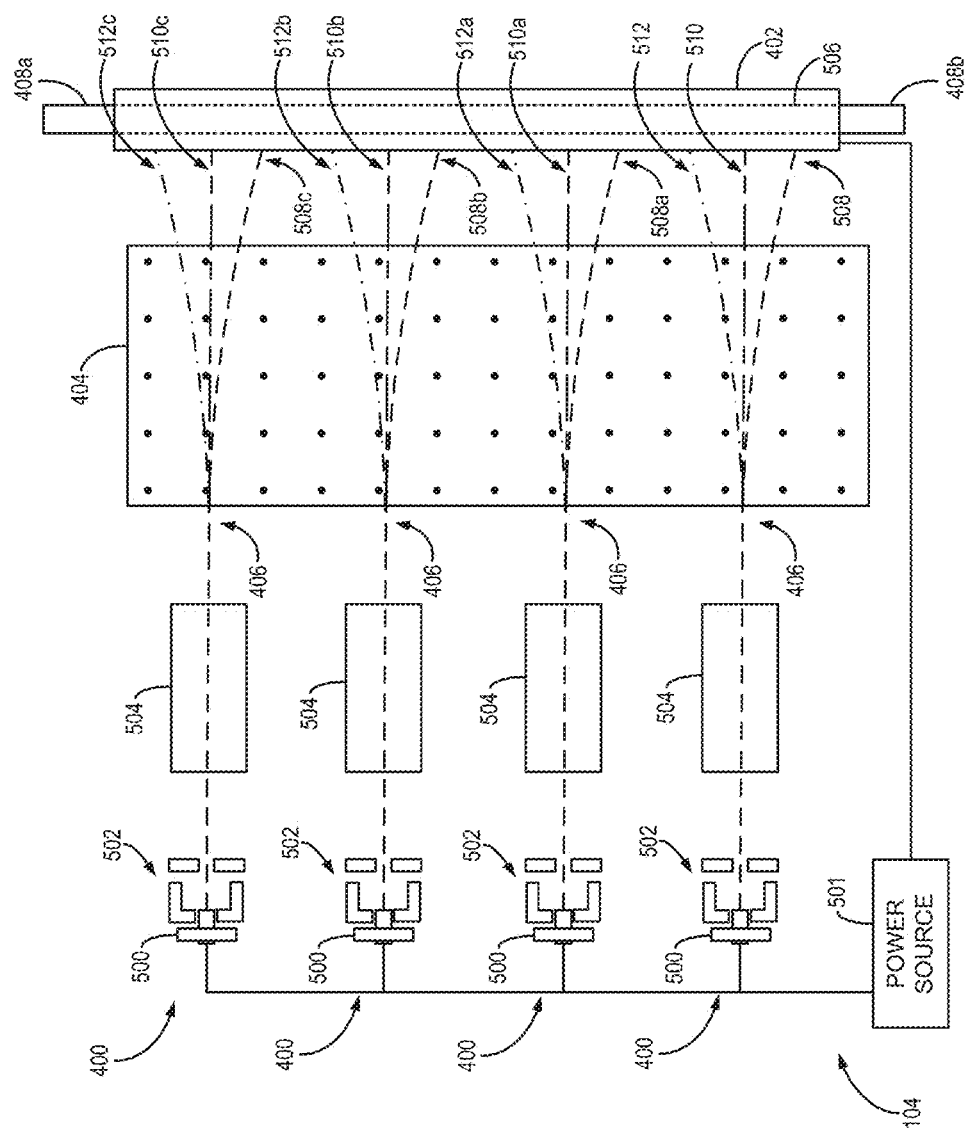
FIG. 5 is a block diagram of the source module of FIG. 4.

Referring to FIG. 5, a schematic illustration is provided that provides a further illustration of the functionality described above. Each electron emitting cathode 500 in the multiple cathodes 400 is powered by a power source 501 and capable of being switched on and off at high frequency by the use of a gate 500 that sits between the emitter 400 and target 402. The power source 501 can be a conventional generator or may be pulser, such as is commercially available from FID GmbH of Burbach, Germany. The electron emitting cathode 500 may be a thermionic, lanthanum hexaboride, or tungsten cathode. Also, it is contemplated that cold cathodes may be used in some situations. One implementation may utilize approximately 2 kV with a wehnelt electrode to serve as the gate 502. Alternatively, grid may be placed a small distance above the cathode 500 surface to act as the gate 502, but with a lower voltage of roughly 500 V.

The beam 406 leaves the cathode 500 and approaches electron optics 504 that are located near the cathode 500. The electron optics 504 both focus the electron beam 406 and allow for a beam shape that is elongated in one direction to control heat loading efficiency on the target 402. In addition, operation and heating of the target 402 may also be controlled by a variety of other functionality. Referring to FIGS. 3-5, the beam 406, though originating at stationary cathodes 400, may be swept across the target 402 using the magnetic deflection system 404. As illustrated in FIG. 3, the target 402 may not be a transmission target and, thus, cooling may be less difficult and can be achieved using some or all of the following techniques. That is, sweeping the beam 406 across the target 402 using the magnetic deflection system 404 can be done to simultaneously achieve two distinct purposes.

First, sweeping or moving the beam 406 to different parts of the target 402 changes the location from which the x-ray beam 302 originates from the source module 104 and is directed to the subject. Thus, despite having a fixed number of cathodes 500 in the cathode array 400, the x-ray beam 302 may be moved without the need to rotate the source module 104 about the subject to move the x-ray beam 302 by moving the beam 406 from a first location 508 to a second location 510 and, then, to a third location 512 on the target 512. By coordinating the movement of all beams 406 that can be created by the array of cathodes 400 and the turning on and off of a given cathode 500 in the array of cathodes 400, the x-ray beam 302 can be moved across the length (L) of the source module 104.

Second, sweeping or moving the beam 406 to different parts of the target 402 allows the target 402 to cool without the need to rotate the target 402. As one non-limiting example, the operation of the cathodes 500 and gates 502 may be coordinated such that the beam 406 moves through the following locations: 508, 508a, 508b, 508c, 510, 510a, 510b, 510c, 512, 512a, 512b, 512c. Such an operation provides a great temporal shift between the beam 406 being directed to location 508. Of course, many other strategies may be employed. As another non-limiting example, multiple locations on the target 402 may be targeted at the same time by firing multiple cathodes 500 simultaneously. However, even when multiple cathodes 500 fire simultaneously, a sweeping strategy may be used and/or interleaved firings may be used to allow the target 402 to cool.

In addition to cooling the target 402 using a sweeping strategy, other cooling systems and methods may be utilized, including the passing of a working fluid from a coolant inlet 408a to a coolant outlet 408b through a path 506 that extends through the target 402. That is, the target 402 may be actively cooled, for example, using the cooling ports 408 to deliver a working fluid, such as an oil, through the inlet 408a and cycle to the outlet 408b. In addition to the illustrated configuration, the coolant inlet 408a and coolant outlet 408b may be arranged to extend through the chamber 403, but at a point where the target 402 is attached to the chamber 403. In this regard, the path 506 does not need to extend through the interior of chamber 403, where the vacuum is maintained.

The cooling ports 408 may also be used for electrical connections. For example, the high voltage connection to the target 402 may also extend through the inlet 408a or outlet 408b, and efficiently utilize the oil as an insulator. Also, the target 402 may be grounded. As such, the cathodes 400 may be insulated and float at, for example, −80 kV. Additionally or alternatively, the cathodes 400 may be cooled, for example, through a cooling port 409. If using the cooling port 409 to supply active cooling to the cathodes 400, the cooling port 409 may also be used to supply the potential to the cathodes 400.

There are many advantages to the above-described configuration. By avoiding rotation of the target 402, it is mechanically simpler and easier to manufacture. Making one large stationary target 402 per module 104 is cost efficient, and also allows active cooling, for example with oil. With oil circulating through the target 402 using the cooling path 506, the x-ray module 104 can be run at higher power than traditional systems that do not have active cooling systems utilizing working fluids. Ultimately, the design offers a practical approach to creating a line or non-linear x-ray source that can deliver an arbitrary number of focal spots by manipulating the path of the beam 406 using the magnetic deflection system 404.

Previous attempts at creating a multi-source x-ray tube have typically involved enormous vacuum chambers at high cost, or a large number of focal spots at fixed positions. The above-described modular design yields an unlimited number of focal spot positions around the patient, with a compact and low cost design that can be used in many applications. When adding one or more of the above-described active-cooling systems, the system can operate at efficiency levels not previously recognized. For example, by rapidly pulsing the cathodes at varying locations on the target, instantaneous heat loads in excess of 100 kW can be supported. In particular, a 100 kW tube can be realized using pulses on the order of 15 microseconds. By triggering sources at varying spatial positions and changing this focal spot position via magnetic deflection, the heat is spread out over the target without mechanically rotating the target. By enabling more than one cathode at a time, even higher instantaneous powers may be produced from each module by a factor of two or more. Furthermore, a stationary target allows for an active cooling system to take this heat from the target to the chiller. Whereas most modern day tubes rely on the inefficient process of radiation to eliminate energy from the target, the current system can place the burden on the chiller, which can be readily scaled as needed.

Referring to FIGS. 2B and 3, imaging of the subject 112 may be performed by arranging the source modules 104 about the subject 112 as illustrated in FIG. 2. In this arrangement, the subject 112 is surrounded by arrays of cathodes 400 per source module 104. The array of cathodes 400 may be arranged as a linear array, as illustrated. Alternatively, as described, the source module 104 may be curved or have a non-linear geometry and, thus, the array of cathodes 400 and the associated components may follow a complementary geometry.

During operation, the source modules 104 can be fired in accordance with any of a wide variety of scanning protocols. For example, multiple source modules 104 can be fired simultaneously. Additionally or alternatively, a given source module 104 can fire multiple cathodes 400 simultaneously or sequentially. Further still, particular modules 104 or even particular cathodes in the array of cathodes 400 may be configured to generate an x-ray beam at one energy, while other modules 104 or even other cathodes in the array of cathodes 400 are configured to generate an x-ray beam at a different energy. In this regard, the system may operate in to perform a dual or other multi-energy imaging process.

As a further example, for applications like cardiac CT, the superior temporal resolution provided by the above-described system enables doctors to make a more accurate diagnosis of heart disease in low to medium risk patients. The best temporal resolution offered today without use of beta blockers or cardiac gating is approximately 75 ms, and this utilizes two x-ray tubes and a half rotation scan. The current tube is able to achieve a temporal resolution better than 25 ms with a full rotation scan. Sequential firing of the sources can achieve at least 25 ms, while turning multiple sources on at one time reduces this time down to the single digits of milliseconds. By utilizing a half rotation scan, the aforementioned times would roughly be cut in half. In the standard single row or multi-row geometry of CT, images with better temporal resolution can be achieved by rotating the x-ray tube and detector around the patient at a faster rate. The maximum rate at which an x-ray tube and detector can be rotated around the patient is limited by the mechanical stresses that are placed on the gantry during such rotation. Current stresses exceed 30 g's and grow with the square of the tangential velocity, meaning that cutting the rotation time in half would result in over 120 g's on the gantry. Incorporating the above-described modules into a multi-source CT scanner, such as illustrated in FIGS. 2A and 2B, provides a system that is free of the rotating gantry. The x-ray tubes that can be triggered electronically enable higher temporal resolution for computed tomography angiography than could be achieved by the rotating gantry of traditional CT systems.

Referring to FIGS. 3 and 5, the above-described system may be utilized to perform a single photon imaging process. That is, the gates 502 may be controlled based on feedback from the detector 108 to control the source module 108 based on the number of photons detected by the detector 108 and, as such, strictly control the dose received by the patient. In this case, the detector 108 may be a photon counting detector, as compared to an energy integrating detector, and, upon receiving feedback from the detector 108 of having received a predetermined number of photons, the cathodes 400 controlled to discontinue the x-ray beam 302. In this situation, it is also contemplated that the detector 108 may have energy discrimination capabilities to further control the dose received by the patient.

Figure 6:
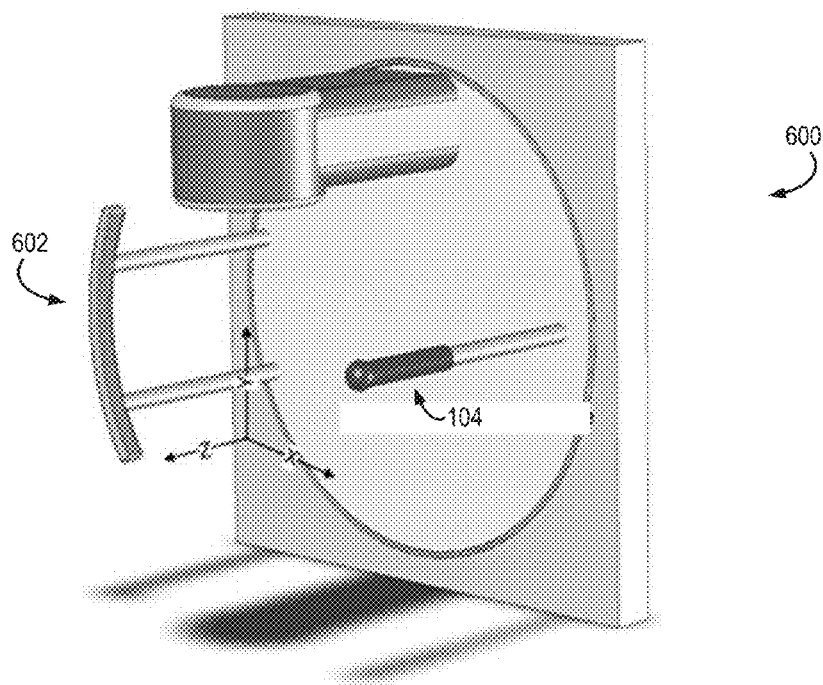
FIG. 6 is a perspective illustration of a tetrahedron beam CT (TBCT) system configured in accordance with the present disclosure.

As another example, referring to FIG. 6, the above-described module 104 may be used in a tetrahedron beam CT (TBCT) system 600. For example, one implementation of TBCT is described in Zhang T, Schulze D, Xu X, Kim J. Tetrahedron beam computed tomography (TBCT): a new design of volumetric CT system. Physics in Medicine and Biology. 2009; 54(11):3365-3378, which is incorporated herein by reference in its entirety. Generally, TBCT utilizes a linear x-ray source to increase image quality in cone beam CT. The linear x-ray source may be delivered by the above-described module 104. Scatter radiation is drastically reduced in TBCT by using a line source x-ray tube and a linear detector 602 oriented perpendicular to each other. By re-binning the data, the same volume is covered as in standard cone-beam CT, but scatter radiation is reduced to produce much better images. While prior-art TBCT systems have demonstrated with a multi-source x-ray tube, the demonstrated systems failed to deliver the necessary current to give the images a high enough signal-to-noise ratio (SNR) to be clinically viable. For example, the system demonstrated by Zhang et al. (Tetrahedron beam computed tomography (TBCT): a new design of volumetric CT system) utilized carbon nanotube cold cathodes and was only capable of producing a current of a few mA. Larger currents have been produced by cold cathodes but in general it is very difficult to produce a high current, long life, and sufficiently large electron beam from cold cathodes due to manufacturing imperfections. By using the module 104 described herein, over 100 times the current that was produced in such x-ray tube attempts can be delivered and, thus, make TBCT clinically viable. The above-described TBCT system 600 may be particularly useful in a variety of clinical settings, including radiotherapy applications.

Figure 7:
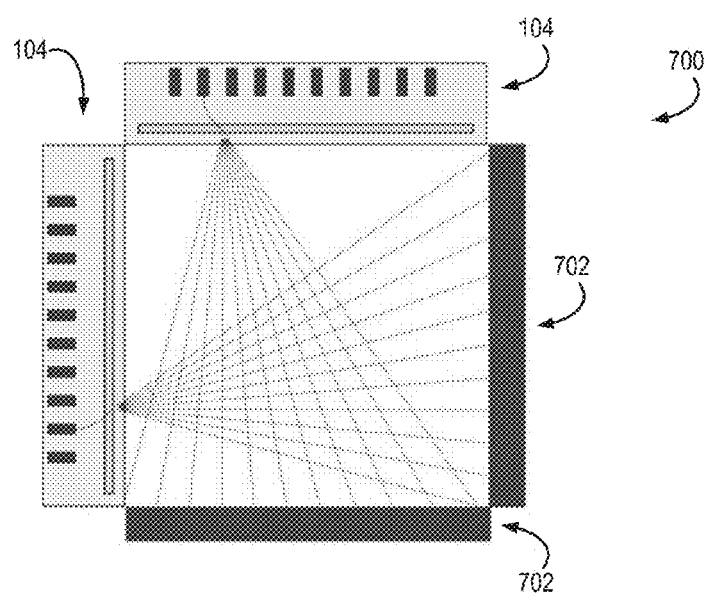
FIG. 7 is schematic illustration of a ultra high-speed imaging system configured in accordance with the present disclosure.

Referring to FIG. 7, a nano-second CT scanner 700 may utilize the multi-source x-ray module 104 and a streak detector 702. In 2013, Gonzales et al. explored in Rectangular computed tomography using a stationary array of CNT emitters: initial experimental results", Proc. SPIE 8668, Medical Imaging 2013: Physics of Medical Imaging, 86685K (Mar. 6, 2013), which is incorporated herein by reference in its entirety, the possibility of using two linear multi-source x-ray tubes opposite two cesium iodide CT detectors to create a CT image from essentially a rectangular geometry. They successfully showed that this technique could be used in high throughput scanning for security purposes. The system described by Gonzales et al. can be substantially improved with better x-ray tubes and faster detectors, both of which are achieved in the multi-source x-ray module 104 of the present disclosure. That is, Gonzales et al. used a multi-source tube that had a limited number of focal spots and ran at low current (7 mA). On the other hand, the multi-source x-ray module 104 described above provides unlimited focal spot positions for more views (hence, fewer artifacts) and higher current. In addition, by positioning streak detectors 702 opposite the multi-source x-ray module 104, nano-second time resolution can be achieved. As such this nano-second CT scanner 700 incorporating the multi-source x-ray module 104 of the present disclosure is the world's fastest CT scanner. This has particular value, for example, in defense applications and ballistic analysis of hypervelocity projectiles and impact analysis. Furthermore, this has particular value when seeking to image and analyze high speed parts, such as turbine blades.

Additionally, the multi-source x-ray module 104 is well suited to dual energy CT implementations. For example, an entire module 104 may be held at a different voltage from an adjacent module, or each cathode 400a-400j within a module 104 may be pulsed to a different high voltage. This multitude of acceleration voltages provides for a range of possible x-ray energies that can be emitted from the target 402. Dual energy CT can be used to reveal the chemical structure of different tissues and to increase contrast. For example, dual energy CT may provide physicians with more information about the mineral content of kidney stones, or be used to remove bone from images to better visualize soft tissue.

In another configuration, multiple electron emitters 400a-400j within multiple modules 104 can be simultaneously activated and swept across the respective targets 402. By modulating the frequency, phase, amplitude or shape of the electron current within in each x-ray generator, each x-ray beam is uniquely encoded. The primary x-radiation from multiple x-ray generators is then detected by at least one detector in a corresponding ring of detectors. An algorithm can uniquely identify which x-ray source hit a corresponding x-ray detector and the relative contribution from each x-ray generator. By simultaneously activating multiple x-ray generators, the time required to obtain a high quality image can be further reduced.

Thus, the modular x-ray tube has been described with multiple sources, each of which deflects to trace out a line source. The system can achieve scanning patterns to improve heat loading, make efficient use of source downtime, and minimize the number of cathodes. A small number of cathodes can be electronically pulsed to emit high current. The electron beams can be focused electrostatically and magnetically deflected to trace out a line or arc on a single cooled target that is attached via ceramics to the chamber. Magnetic shielding can be used to limit the deflection region. By making the system modular, a smaller chamber is needed, resulting in a better vacuum and a system that is easier to build. The magnets may be placed outside the chamber to keep the chamber small and simplify manufacturing. This x-source provides an unlimited number of focal spot positions. The tube can be used for multiple applications, including ultra high-speed imaging, lower dose applications, and large volume imaging. That is, the present disclosure provides a system and method that reduces dose or Artifacts by controlling scatter in large volume imaging and by allowing use of a virtual bowtie. Furthermore, the present disclosure provides a system that can be realized as a mobile high speed imaging system that includes 2 tubes and 2 detectors and or an ultra high speed CT scanner, such as is advantageous for cardiac CT and nanosecond CT applications.

The above described systems and methods may be adapted for any of a variety of settings, applications, and configurations. For example, the target 402 could be reduced in size and rotated for some configurations. Furthermore, the above-described systems and methods may be adapted to work within existing systems or integrated with a variety of medical systems to improve various systems and methods. As a non-limiting example, the above-described systems and methods may be integrated or retrofitted to become part of a radiation therapy system.

Figure 8:
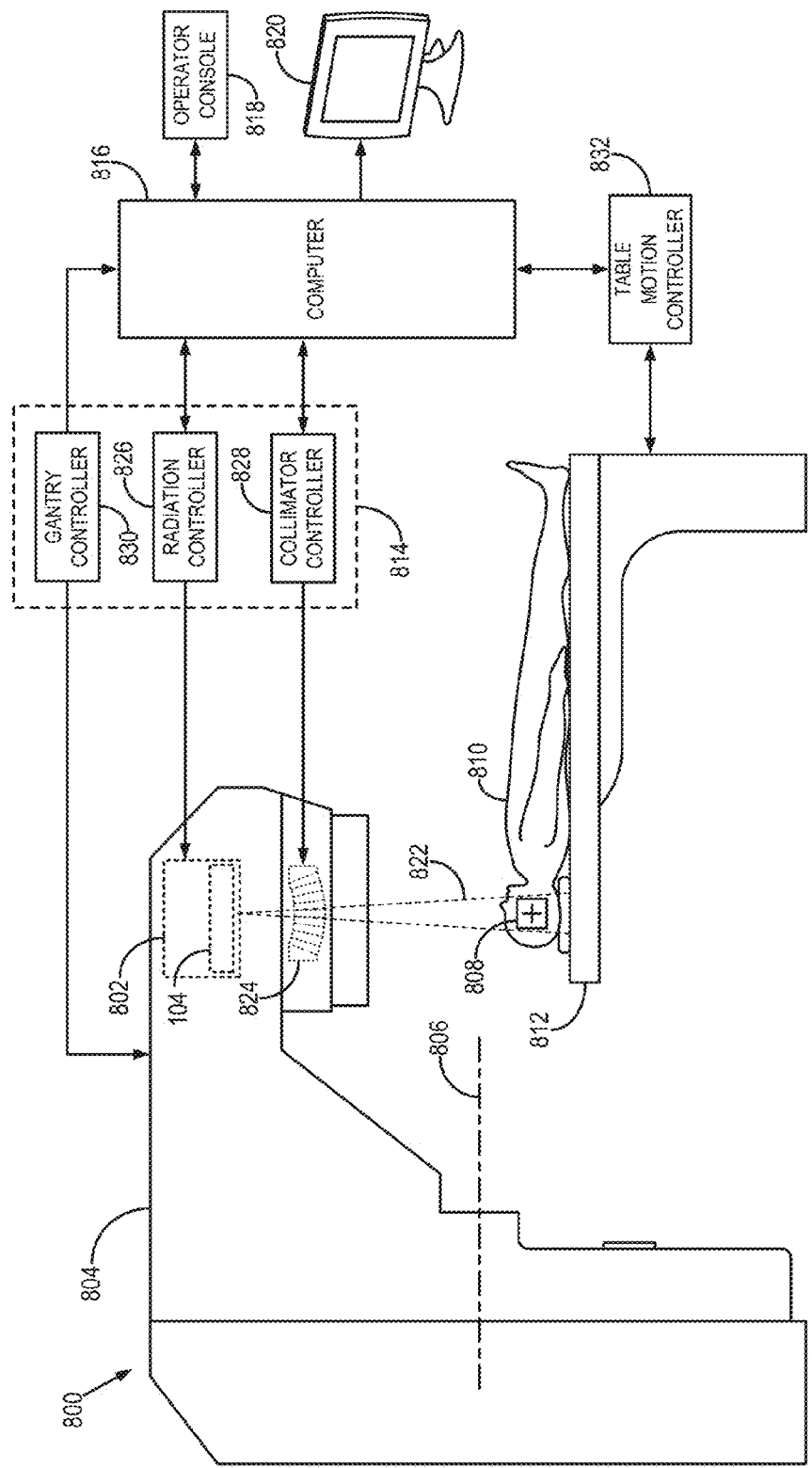
FIG. 8 is a schematic illustration of a radiation therapy system in accordance with the present disclosure.

For example, referring to FIG. 8, an example of an intensity-modulated arc therapy ("IMAT") system 800 is illustrated that may include a radiation source 802 that incorporates one or more of the above-described x-ray source module 104, which is housed at an end of a rotatable gantry 804 that rotates about a rotation axis 806. The rotatable gantry 804 allows the radiation source 802 to be aligned in a desired manner with respect to a target volume 808 in a subject 810 positioned on a patient table 812. A control mechanism 814 controls the rotation of the gantry 804 and the delivery of radiation from the radiation source 802 to the target volume 808. The IMAT system 800 includes a computer 816 that receives commands and scanning parameters from an operator via a console 818, or from a memory or other suitable storage medium. An associated display 820 allows the operator to observe data from the computer 816, including images of the subject 810 that may be used to review or modify the treatment plan, and to position the subject 810 by way of appropriately adjusting the position of the patient table 812. The operator supplied commands and parameters may also be used by the computer 816 to provide control signals and information to the control mechanism 814.

The radiation source 802 produces a radiation beam 822, or "field," that is directed to the subject 810. The radiation source 802, as described may include one or more source modules 104. The one or more source modules 104 may be used only for imaging to guide the radiation therapy process. Additionally or alternatively, the one or more source modules 104 may deliver the radiation beam 822 to deliver the therapeutic radiation. If the one or more source modules 104 are used to deliver the radiation beam 822 to deliver the therapeutic radiation, the radiation beam 822 may be modulated as described above, for example, by switching gates on and off or sweeping the beam across the target or activating and deactivating modules. Thus, a collimator 824 is not necessary, but may optionally be included, particularly, if the one or more source modules 104 is designed only to perform imaging to guide the radiation therapy process. If included, the collimator 824 may include a multileaf collimator that is composed of a plurality of independently adjustable collimator leaves. In such a configuration, each leaf in the collimator 824 is composed of an appropriate material that inhibits the transmission of radiation, such as a dense radioopaque material, and may include lead, tungsten, cerium, tantalum, or related alloys.

The one or more source modules 104 are mounted on a rotatable gantry 804 that rotates about a rotation axis 806 so that the radiation beam 822 may irradiate the target volume 808 in the subject 810 from a variety of gantry angles, $\theta_i$. The radiation source 802 is controlled by a radiation controller 826 that forms a part of the control mechanism 814, and which provides power and timing signals to the radiation source 802.

A collimator controller 828, which forms a part of the control mechanism 814, controls the movement of each of the collimator leaves in and out of its corresponding sleeve. The collimator controller 828 moves the collimator leaves rapidly between their open and closed states to adjust the aperture shape of the collimator 824 and, therefore, the shape and fluence of the radiation beam 822. The collimator controller 828 receives instructions from the computer 816 to allow program control of the collimator 824.

A gantry controller 830, which forms a part of the control mechanism 814, provides the signals necessary to rotate the gantry 804 and, hence, to change the position of the radiation source 802 and the gantry angle, $\theta_i$, of the radiation beam 822 for the radiation therapy. The gantry controller 830 connects with the computer 816 so that the gantry 804 may be rotated under computer control, and also to provide the computer 816 with a signals indicating the gantry angle, $\theta_i$, to assist in that control. The position of the patient table 812 may also be adjusted to change the position of the target volume 808 with respect to the radiation source 802 by way of a table motion controller 832, which is in communication with the computer 816.

During operation of the IMAT system 800, the collimator controller 828 receives, from the computer 816, segmentation information indicating the aperture shape to be used for each gantry angle, $\theta_i$, during each sweep of the radiation source 802. The segmentations describe the intensity of the radiation beam 822 that is desired for each gantry angle, $\theta_i$.

The present invention has been described in terms of one or more preferred embodiments, and it should be appreciated that many equivalents, alternatives, variations, and modifications, aside from those expressly stated, are possible and within the scope of the invention. Features suitable for combinations and sub-combinations would be readily apparent to persons skilled in the art upon review of the present application as a whole. The subject matter described herein and in the recited claims intends to cover and embrace all suitable changes in technology.

As used in the claims, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The invention claimed is:

1. An imaging system comprising:
    a platform for receiving a subject to be imaged using the imaging system;
    a source module arranged to deliver a beam of ionizing radiation to the subject, the source module comprising:
        a vacuum chamber;
        a plurality of cathodes and respective gates, each cathode configured to generate a separate beam of electrons directed across the vacuum chamber and each gate matched to at least one respective cathode to enable and disable each separate beam of electrons from being directed across the vacuum chamber;
        a target anode arranged to receive the separate beam of electrons from each of the plurality of cathodes and, therefrom, generate the beam of ionizing radiation;
        a deflection system arranged between the plurality of cathodes and the target anode to generate a variable magnetic field to control a path followed by each of the separate beams of electrons to the target anode; and
    a controller configured to control operation of the plurality of cathodes and respective gates to selectively enable and disable each separate beam of electrons from being directed across the vacuum chamber and control operation of the deflection system to change the path followed by each of the separate beam of electrons to the target anode based on a heating of the target anode caused by the beam of electrons.

2. The system of claim 1 wherein the deflection system includes at least one deflection coil configured to create a variable magnetic field to control the path followed by each of the separate beams of electrons to sweep across the target anode.

3. The system of claim 1 wherein the target anode is in a fixed position.

4. An imaging system comprising:
    a platform for receiving a subject to be imaged using the imaging system;
    a source module arranged to deliver a beam of ionizing radiation to the subject, the source module comprising:
        a vacuum chamber;
        a plurality of cathodes and respective gates, each cathode configured to generate a separate beam of electrons directed across the vacuum chamber and each gate matched to at least one respective cathode to enable and disable each separate beam of electrons from being directed across the vacuum chamber;
        a target anode arranged to receive the separate beam of electrons from each of the plurality of cathodes and, therefrom, generate the beam of ionizing radiation;
        a deflection system arranged between the plurality of cathodes and the target anode to generate a variable magnetic field to control a path followed by each of the separate beams of electrons to the target anode;
        a controller configured to control operation of the plurality of cathodes and respective gates to selectively enable and disable each separate beam of electrons from being directed across the vacuum chamber and control operation of the deflection system to change the path followed by each of the separate beam of electrons to the target anode based on at least one of a heating of the target anode caused by the beam of electrons and a view angle of the subject to be achieved using the ionizing radiation; and
    wherein the target anode is an elongated pane having a tapered surface that directs the ionizing radiation away from the target anode toward the subject and generally orthogonally to the path followed by each of the separate beams of electrons to the target anode.

5. The system of claim 1 further comprising a bore having a plurality of source modules having a linear or an arcuate geometry arranged thereabout.

6. The system of claim 1 further comprising a cooling path that extends through the vacuum chamber and the target anode from a coolant inlet to a coolant outlet to receive a working fluid to flow therethrough and actively cool the target anode.

7. The system of claim 6 further comprising at least one electrical connection extending into the vacuum chamber through one of the coolant inlet and the coolant outlet.

8. The system of claim 1 wherein the controller is configured to control the plurality of cathodes and respective gates to enable multiple of the separate beams of electrons simultaneously.

9. The system of claim 1 wherein the source module is configured to deliver the ionizing radiation to the subject at multiple energies to perform a multi-energy imaging process.

10. The system of claim 1 further comprising focusing optics arranged in the vacuum chamber to beam shape each of the separate beams of electrons to control heat loading efficiency on the target anode.

11. The system of claim 1 wherein the controller is configured to control operation of the source module according to a virtual bowtie protocol by modulating at least one of time, energy, and/or intensity of the ionizing radiation.

12. The system of claim 1 wherein the imaging system forms at least part of one of a computed tomography (CT) system, a radiation therapy system, a tetrahedron beam CT (TBCT) system, and/or a high-speed imaging system.

13. An imaging system comprising:
    a bore for receiving a subject to be imaged using the imaging system;

a plurality of source modules arranged about the bore to deliver a beam of x-rays to a subject to be imaged, each source module comprising:
a vacuum chamber;
a plurality of cathodes and respective gates, each cathode configured to generate a separate beam of electrons directed across the vacuum chamber and each gate matched to at least one respective cathode to enable and disable each separate beam of electrons from being directed across the vacuum chamber;
a target anode arranged to receive the separate beam of electrons from each of the plurality of cathodes and, therefrom, generate the beam of x-rays;
a deflection system arranged between the plurality of cathodes and the target anode to generate a variable magnetic field to control a path followed by each of the separate beams of electrons to the target anode;
a controller configured to control operation of the plurality of cathodes and respective gates to selectively enable and disable each separate beam of electrons from being directed across the vacuum chamber and control operation of the deflection system to change the path followed by each of the separate beam of electrons to the target anode based on a heating of the target anode caused by the beam of electrons; and
a plurality of detectors arranged in opposition to a respective one of the plurality of source modules across the bore to receive the beam of x-rays and assembled medical imaging data based thereon.

14. A source module for generating x-rays comprising:
a vacuum chamber;
a plurality of cathodes and respective gates, each cathode configured to generate a separate beam of electrons directed across the vacuum chamber and each gate matched to at least one respective cathode to enable and disable each separate beam of electrons from being directed across the vacuum chamber;
a stationary target anode fixed within the vacuum chamber and arranged to receive the separate beam of electrons from each of the plurality of cathodes and, therefrom, generate a beam of x-rays; and
a deflection system arranged between the plurality of cathodes and the stationary target anode to generate a variable magnetic field to control a path followed by each of the separate beams of electrons to the stationary target anode to selectively sweep across the stationary target anode and, thereby, change a point of impact of each separate beam of electrons with the stationary target anode and change a location of the beam of x-rays generated.

15. The source module of claim 14 wherein the deflection system includes at least one deflection coil configured to create a variable magnetic field to control the path followed by each of the separate beams of electrons to sweep across the stationary target anode.

16. The source module of claim 14 wherein the deflection system includes a pair of deflection coils arranged on opposing sides of the path followed by each of the separate beams of electrons to sweep across the stationary target anode by drawing each of the separate beams of electrons to or opposing each of the separate beams of electrons from each of the pair of deflection coils.

17. A source module for generating x-rays comprising:
a vacuum chamber;
a plurality of cathodes and respective gates, each cathode configured to generate a separate beam of electrons directed across the vacuum chamber and each gate matched to at least one respective cathode to enable and disable each separate beam of electrons from being directed across the vacuum chamber;
a target anode fixed within the vacuum chamber and arranged to receive the separate beam of electrons from each of the plurality of cathodes and, therefrom, generate a beam of x-rays; and
a deflection system arranged between the plurality of cathodes and the target anode to generate a variable magnetic field to control a path followed by each of the separate beams of electrons to the target anode to selectively sweep across the target anode and, thereby, change a point of impact of each separate beam of electrons with the target anode and change a location of the beam of x-rays generated; and
wherein the target anode forms an elongated pane or an arcuate pane having a tapered surface that directs the beam of x-rays away from the target anode and generally orthogonally to the path followed by each of the separate beams of electrons to the target anode.

18. The source module of claim 14 further comprising a cooling path that extends through the vacuum chamber and the stationary target anode from a coolant inlet to a coolant outlet to receive a working fluid to flow therethrough and actively cool the stationary target anode.

19. The system of claim 14 further comprising a cooling path configured to deliver a working fluid through the vacuum chamber to cool the plurality of cathodes.

20. The system of claim 14 further comprising focusing optics arranged in the vacuum chamber to beam shape each of the separate beams of electrons to control heat loading efficiency on the stationary target anode.

21. The system of claim 1 wherein the target anode is stationary.

22. The system of claim 4 wherein the target anode is stationary.

23. The system of claim 13 wherein the target anode is stationary.

24. The system of claim 17 wherein the target anode is stationary.

* * * * *